United States Patent [19]

Chiang

[11] Patent Number: 4,843,013

[45] Date of Patent: * Jun. 27, 1989

[54] MULTIPLE CONTROL STANDARD FOR BLOOD ANALYSIS

[75] Inventor: Ching Chiang, Acton, Mass.

[73] Assignee: Bionostics, Incorporated, Acton, Mass.

[*] Notice: The portion of the term of this patent subsequent to Jun. 28, 2005 has been disclaimed.

[21] Appl. No.: 163,330

[22] Filed: Mar. 2, 1988

Related U.S. Application Data

[63] Continuation-in-part of Ser. No. 849,758, Apr. 9, 1986, Pat. No. 4,753,888.

[51] Int. Cl.$^4$ .............................................. G01N 33/00
[52] U.S. Cl. ............................................. 436/11; 436/8; 436/9; 436/18; 436/19; 436/15
[58] Field of Search ................................. 436/8–19, 436/66–68; 252/408.1; 378/48; 514/6; 356/39–42

[56] References Cited

U.S. PATENT DOCUMENTS

| | | | |
|---|---|---|---|
| 4,141,856 | 2/1979 | Dorwart et al. | 436/11 |
| 4,151,108 | 8/1979 | Sorensen et al. | 436/11 |
| 4,163,734 | 8/1979 | Sorensen et al. | 436/11 |
| 4,279,775 | 7/1981 | Louderback et al. | 436/11 |
| 4,299,728 | 11/1981 | Cormier et al. | . |
| 4,363,633 | 12/1982 | Christiansen | 436/19 |
| 4,369,127 | 1/1983 | Cormier et al. | . |

OTHER PUBLICATIONS

Ramieri, A. Jr., Jatlow P., and Seligson D., *New Method for Rapid Determination of Carboxyhemoglobin by Use of Double-Wavelength Spectrophotometry*, Clin. Chem. vol. 20 No. 2 278–281 (1974).

AS Siggaard-Andersen O., Norgaard-Pedersen B., and Rem J., Hemoglobin Pigments. *Spectrophotometric Determination of Oxy-, Carboxy-, Met-, and Sulfhemoglobin in Capillary Blood.* Clin. Chim. Acta, 42, 85–100 (1972).

Zwart A., Buursma A., Oeseburg B., and Zijilstra W. S., *Determination of Hemoglobin Derivatives with the IL 282CO-Oximeter as Compared with a Manual Spectrophotometric 5-Wavelength Method.* Clin. Chem. vol. 27 No. 11 (1981).

Zwart A., Buursma A., van Kampen E. J., Oeseburg B., van der Ploeg P. H. W., and Zijlstra W. G., *A Multi-Wavelength Spectrophotometric Method for the Simultaneous Determination of 5 Haemoglobin Derivatives* J. Clin. Chem. Clin. Biochem vol. 19 457–463 (1981).

*Primary Examiner*—Barry S. Richman
*Assistant Examiner*—T. J. Wallen
*Attorney, Agent, or Firm*—Hamilton, Brook, Smith & Reynolds

[57] ABSTRACT

This invention discloses a multiple control standard for the use in the quality assurance of blood analysis instrumentation systems. The liquid control standard is able to act as a control standard for blood gas instrumentation systems measuring pH, pCO2 and pO$_2$ of blood, as a control standard for a co-oximeter measuring the amount of total hemoglobin present in the blood and the relative amounts of other hemoglobin fractions present in the blood, and as a liquid control standard for ion selective electrode instrumentation systems for the measuring of electrolytes such as Na, K, Li and Ca ions in the blood.

7 Claims, No Drawings

MULTIPLE CONTROL STANDARD FOR BLOOD ANALYSIS

This application is a continuation-in-part of U.S. Ser. No. 849,758 filed Apr. 9, 1986; now U.S. Pat. No. 4,753,888, issued June 28, 1988.

BACKGROUND OF THE INVENTION

Clinical laboratories employ a variety of instrumentation systems for the analysis of patient samples. Frequently, three types of instruments are used to analyze particularly significant properties of fresh blood for diagnosis of respiratory-pulmonary ailments. These instruments are:

1. pH/blood gas instruments - measures blood pH, $pCO_2$ and $pO_2$.
2. Co-oximeter instruments - measures total hemoglobin, oxyhemoglobin, carboxyhemoglobin and methemoglobin.
3. ISE Electrolyte instruments - measures electrolyte (such as sodium, potassium, lithium and calcium) content of blood.

It is common practice to employ control solutions for verifying the accuracy and reliability of these instrumentation systems. A different control solution is used for each instrument. For example, a separate and distinct control solution is used to test the blood gas analyzer. A separate and distinct control solution is used to test the co-oximeter and a third separate and distinct solution is needed to test the ion analyzer. In other words, most pH/blood gas control materials serve as controls only for pH, $pCO_2$ and $pO_2$. One of the blood gas controls that is formulated with stabilized red blood cells does provide control values for total hemoglobin and the other hemoglobin fractions but not for electrolyte vlaues.

Controls for hemoglobin fractions for use with co-oximetry instrumentation systems do not provide parameters for use as controls with pH/blood gas analyzers or for ISE electrolyte analyzers. Similarly, controls for ISE instrumentation are not useable for either pH/blood gas or co-oximetry instruments (in addition, some controls contain preservatives or other ingredients which make the material unsuitable for use in another type of instrument).

SUMMARY OF THE INVENTION

This invention discloses a synthetic control solution which provides control parameters for three types of instrument systems: pH/blood gas, co-oximeters and ISE electrolytes instruments.

The synthetic liquid control is comprised of an aqueous solution buffered to a pH of from about 7.1 to 7.7 and containing sufficient bicarbonate ion to provide a $pCO_2$ of from about 15 to about 80 after subsequently equilibrated with the desired levels of gaseous carbon dioxide, gaseous oxygen to provide a $pO_2$ of from about 50 to 400, absorbance means to provide measurements of several hemoglobin fractions and salts of ions to provide measurements of these ions in solution.

DETAILED DESCRIPTION OF THE INVENTION

This invention discloses a synthetic liquid control standard comprised of an aqueous solution buffered to a pH of from about 7.1 to about 7.7 and containing sufficient bicarbonate ion to provide a $pCO_2$ of from about 15 to about 80 after subsequently equilibrated with the desired levels of gaseous carbon dioxide, gaseous oxygen to provide a $pO_2$ of from about 50 to about 400, absorbance means to provide measurements of total hemoglobin and of several hemoglobin fractions, and sodium, potassium, lithium and calcium salts to provide measurements of these ions in solution.

In order to provide the desired pH for the respective normal, acidosis or alkalosis conditions, a buffer material should be selected which has a $pK_a$ close to the desired working pH. A particularly useful buffer material for providing the desired pH conditions in the control solution of this invention is N-2-hydroxyethylpiperazine-N'-2-ethanesulfonic acid (HEPES) which has a $pK_a$ of 7.31 at 37° C. Other suitable buffer materials are, for example, N-tris(hydroxymethyl)methyl-2-aminoethanesulfonic acid (TES), which has a $pK_a$ of 7.16 at 37° C.; 3-(N-morpholino) propanesulfonic acis (MOPS), which has a $pK_a$ of 7.01 at 37° C.; and Tri-(Hydroxymethyl) aminomethane (TRIS) which has a $pK_a$ of 7.77 at 37° C. These and other such suitable buffer materials, including the sodium salt derivatives, are described by Good et al. Biochemistry 5, 467–77 (1966) and Ferguson et al., Analytical Biochemistry 104, 300–310 (1980), the teachings of which are hereby incorporated by reference.

The desired $pCO_2$ level is provided in part by addition of bicarbonate ion, for example, $NaHCO_3$, to the aqueous solution that a $pCO_2$ of from about 15 to about 80 is reached after subsequently equilibrated with the desired levels of gaseous carbon dioxide. The desired $pO_2$ level of from about 50 to about 400 is facilitated by addition of gaseous oxygen to the solution or the head space in the receptacle containing the aqueous solution. Addition of gaseous carbon dioxide similarly can facilitate maintenance of the aforesaid desired $pCO_2$ levels.

In a typical co-oximeter, a whole blood sample is aspirated into the instrument, mixed with diluent, hemolyzed, and brought to a constant temperature in a cuvette. A microcomputer calculates the total hemoglobin concentration present, expressed in grams per one hundred milliliters of whole blood g/dL THb. A typical co-oximeter also measures the percent oxyhemoglobin ($O_2Hb$), carboxyhemoglobin (COHb), methemoglbin (MetHb), and reduced hemoglobin. Each of these species of hemoglobin will absorb light at different wavelengths along the 500–650 nm range.

The control solution of the present invention contains absorbance means, such as dyes, which can absorb light in the 500–650 nm range at approximately the same percentage and wavelength as predetermined concentrations of the different hemoglobin species. By using this control solution with the co-oximeter, it can be determined whether or not the co-oximeter is functioning properly and whether or not the instrument needs to be recalibrated.

The absorbance means need not absorb light exactly as the different species of hemoglobin do. What is important is that a relationship can be determined such that the light absorbed by the absorbance means in the control solution can be correlated to a specific absorbance level of the particular hemoglobin species in question.

In a preferred embodiment, the control solution of the present invention contains a combination of Acid Red Dye #27 (CI 16185), Acid Yellow Dye #23 (CI 19140) and Acid Blue Dye #9 (CI 42090). Also used is the combination of Ponceau 3R Red Dye (CI 16155) and Acid BLue Dye (CI 42090).

The blue dye is used because it has a maximum absorbance of light at 630 nm as does methemoglobin.

The red dyes were chosen due to the fact that they show absorbance levels at the 560 nm and 535 nm wavelengths as does oxyhemoglobin, at the 570 nm wavelength as does carboxyhemoglobin, and at the 550 nm wavelength as does reduced hemoglobin. By altering the concentrations of these dyes in the control solution, the control solution can simulate samples of blood having various levels of the different fractions of hemoglobin and of total hemoglobin.

Also contained within the control solution of this invention are predetermined amounts of electrolytes for testing ISE Electrolyte instruments. These electrolytes are placed into solution with constant ionic strength by dissolving the approximate amount of the salts of these electrolytes. The electrolytes most often tested are sodium, potassium, lithium and calcium ions. Therefore, controls having a measurable range of electrolyte values of Na, K, Li and Ca can be made by the addition of appropriate quantities of sodium, potassium, lithium and calcium salts, such as NaCl, KCl, $CaCl_2$ and LiCl.

In a preferred embodiment of this invention, the concentration of Na ions result from the combination of the salts of the acid dyes as well as the addition of NaOH, NaCl, $NaN_3$ and $NaHCO_3$.

The density of the control solution can be placed at 1.01 to 1.03 and the viscosity of the solution from 2 to 4 centipoises which are similar to the density and viscosity of blood by adding up to 70 g/L of natural polymers, such as bovine serum albumin, or one of the synthetic polymers such as Polyethylene glycol (PEG) 8000, Polyvinylpyrrolidone (PVP) 40, Polyvinyl alcohol (PVA) and Ficoll 400. (Ficoll 400 is a synthetic high polymer made by the copolymerization of sucrose and epichlorohydrin produced by the Pharmacia Fine Chemicals AB Company of Uppsala, Sweden. Ficoll 400 indicates that the polymer has a molecular weight of approximately 400,000.)

To ensure a stable long shelf life of more than two years at room temperature, a chemical preservative such as sodium azide or formaldehyde can be added to the solution, or the solution can be sterilized by either membrane filtration or by high temperature sterilization if the solution does not contain the polymers used to increase the viscosity of the solution.

Two preferred formulations are listed below. By varying the concentrations of the reagents in the following formulations a varied number of control standards can be produced. These control standards will then have different levels of pH, $pCO_2$, $pO_2$, total hemoglobin fractions and concentrations of sodium, potassium, lithium and calcium ions. For example, the formulations listed below contain sodium and potassium salts as the electrolyte, however, other formulations can include various combinations of some or all of the previously described electrolyte compositions.

| Formulation I | | | |
|---|---|---|---|
| Compound | Concentration | | |
| HEPES and/or TRIS, MOPS | 20 | to | 100 mM |
| NaCl | 40 | to | 100 |
| KCl | 2 | to | 8 |
| NaOH | 0 | to | 60 |
| $NaHCO_3$ | 18 | to | 26 |
| Acid Red Dye #27 (CI 16185) | 2 | to | 5 |

| Formulation I -continued | | | |
|---|---|---|---|
| Compound | Concentration | | |
| Acid Yellow Dye #23 (CI 19140) | 3 | to | 7 |
| Acid Blue Dye #9 (CI 42090) | 0.015 | to | 0.08 |
| Polymer (PVA, Ficoll 400, PEG 8000, PVP 40 or Bovine serum albumin) | 0 | to | 50 g/l |
| Formulation II | | | |
| HEPES and/or TRIS, MOPS | 20 | to | 100 mM |
| NaCl | 40 | to | 100 |
| KCl | 2 | to | 8 |
| NaOH | 0 | to | 60 |
| $NaHCO_3$ | 18 | to | 26 |
| $NaN_3$ | 0 | to | 40 |
| Formaldehyde | 0 | to | 60 |
| Ponceau 3R Red Dye (CI 16155) | 5 | to | 11 |
| Acid Blue Dye #9 (CI 42090) | 0.015 | to | 0.08 |
| Polymer (PVA, Ficoll 400, PEG 8000 or Bovine serum albumin) | 30 | to | 70 g/l |

Using varying amounts of the reagents from the preferred formulations, three levels of multiple control standards can be formulated, namely Level I Control, Level II Control and Level III Control.

The multiple control standard of Level II simulates normal blood having a pH of about 7.4, a $pCO_2$ of about 40 mm Hg and $pO_2$ of about 100 mm Hg. The multiple control standard of Level II contains a sufficient concentration of dye to simulate a total hemoglobin concentration of about 14 g/100ml of blood. This total hemoglobin reading can be produced by placing red dye, yellow dye and blue dye into solution to give the control standard the ability to absorb the light spectrum in the wavelengths between 400 to 650 nm. The yellow dye is used in order to give the control the appearance of blood but does not absorb light in the critical ranges. A preferred concentration of dyes is about 3.5 mM of Acid Red Dye #27 (CI 16185), about 5 mM of Acid Yellow Dye #23 (CI 19140) and about 0.04 mM of Acid Blue Dye #9 (CI 42090). This concentration of dyes in solution results in a control standard having an appearance of blood and giving a total hemoglobin reading of about 14 grams in 100ml of aqueous solution as measured by the Corning 2500 Co-oximeter, 9 g/100ml by the IL282 Co-oximeter and 26 g/100ml by the ABL-30 Blood Gas Analyser. The multiple control standard of Level II also contains a concentration of sodium ions of about 140mM and a concentration of potassium ion of about 5 mM.

The multiple control standard of Level I simulates blood having a low pH of 7.10 to 7.20, a high $pCO_2$ of from about 60 to 70 mm Hg, and a low $pO_2$ of from about 50 to 65 mm Hg. (This control standard thus simulates acidosis.) The control standard of Level I also contains a low concentration of Na ions from about 115 to 125mM and a low concentration of K ions from about 2.5 to 3.5 mM.

The multiple control standard of Level I also contains a lower concentration of all dyes to simulate a total hemoglobin of about 9g/100ml of blood as read by the Corning 2500 Co-oximeter. A preferred control solution of Level I contains about 2mM of Acid Red Dye #27 (CI 16185), about 3 mM of Yellow Dye #23 (CI 19140), and about 0.015 mM of Acid Blue Dye #9 (CI 42090).

The multiple control standard of Level III simulates a sample of blood having a high pH of about 7.6, a low $pCO_2$ of about 22 mm Hg and a high $pO_2$ level of about 150mm Hg. (This control standard thus simulates alkalosis). The multiple control standard of Level III also contains a sufficient concentration of dyes to simulate a high total hemoglobin of about 18g/100ml of solution. This total hemoglobin reading is produced by having a higher concentration of all dyes, preferably about 5 mM of Acid Red Dye #27 (CI 16185), about 7 mM of Acid Yellow Dye #23 (CI 19149), and about 0.08 mM of Acid Blue Dye #9 (CI 42090). The control standard of Level III also contains a higher concentration of sodium ions 160mM and of potassium ions of about 7 mM.

The desired $pCO_2$ value is provided in part by the addition of bicarbonate ion, e.g. $NaHCO_3$ to the aqueous solution. $CO_2$ gas is then added to the aqueous solution unitl a $pCO_2$ of from about 15 to about 80 mm Hg is attained, depending upon which control level is being produced.

The desired $pO_2$ level of from about 50 to 160mm Hg, depending upon which control level is being produced, is reached by the addition of gaseous oxygen to the solution and head space in the receptacle containing the aqueous solution. Addition of gaseous carbon dioxide similarly can facilitate maintenance of the aforesaid desired $pCO_2$ levels.

The final control standard solution is retained in a sealed or air-tight receptacle such as, for example, a glass vial or ampule to retain the desired gas equilibrium. The head space in the receptacle can be filled with an appropriate gas to facilitate the provision of the aforesaid $pCO_2$ conditions. For example, for the acidosis blood gas control, a mixture of 6.5% oxygen, 5.9% of carbon dioxide and 87.6% of nitrogen is used. For the normal blood gas control a mixture of about 4.1% of carbon dioxide, 11.8% of oxygen and 84.1% of nitrogen is used. For the alkalosis blood gas control a mixture of about 2.3% of carbon dioxide, 18% of oxygen and 79.7% of nitrogen is used. It will be appreciated that any other inert gas can be used as a substitute for part or all of the nitrogen portion of the head space in the foregoing illustrative examples.

The following specific and detailed example will further illustrate the invention although it will be appreciated that this example is not meant to restrict the invention to the specific details found in such example. For example, although the following formulations contain only sodium salt and potassium salt electrolytes, the invention is not intended to be limited as such. Formulations containing electrolytes of lithium salts and calcium salts, either alone or in any combination with the electrolytes described herein are intended to be within the scope of the invention.

EXAMPLE

The blood gas control liquids are preferably formulated to represent three levels of pH, $pCO_2$ and $pO_2$ values to have different combinations of dye concentration that simulate three levels of hemoglobin values and the visual appearance of hemolyzed blood plus three different levels of both sodium and potassium ions.

A preferred embodiment of the invention has the following formulation:

| COMPOUND | CONCENTRATION |
| --- | --- |
| HEPES | 20 to 100 mM |
| NaCl | 40 to 100 mM |
| KCl | 2 to 8 mM |
| NaOH | 20 to 30 mM |
| $NaHCO_3$ | 18 to 26 mM |

Three different buffers were made using HEPES, NaOH, NaCl, KCl and $NaHCO_3$ in different concentrations. They were:

|  | Acidosis (I) | Normal (II) | Alkalosis (III) |
| --- | --- | --- | --- |
| HEPES | 40.0 mM | 40.0 mM | 40.0 mM |
| NaOH | 20.0 | 25.7 | 29.6 |
| KCl | 3.0 | 5.0 | 7.0 |
| NaCl | 73.2 | 81.5 | 99.3 |
| $NaHCO_3$ | 21.3 | 23.9 | 19.4 |

Three different levels of dyes were added to the corresponding buffer solutions.

|  | Acidosis (I) | Normal (II) | Alkalosis (III) |
| --- | --- | --- | --- |
| Red Dye #27 | 2.34 mM | 3.72 mM | 4.84 mM |
| Yellow Dye #23 | 1.57 | 2.6 | 3.39 |
| Blue Dye #9 | 0.016 | 0.04 | 0.08 |

The buffered dye solutions were then separately placed in a container which was thermally controlled to 25° C. The appropriate gas mixture was then bubbled through each solution at a rate of 5 to 7 L/min. until the pH, $pCO_2$, and $pO_2$ reached equilibrium values, as determined by appropriate blood gas analyzers. The gas mixtures used had the following compositions:

|  | Acidosis (I) | Normal (II) | Alkalosis (III) |
| --- | --- | --- | --- |
| $CO_2$ | 6.5% | 4.1% | 2.3% |
| $O_2$ | 5.9 | 11.8 | 18.0 |
| $N_2$ | 87.6 | 84.1 | 79.7 |

After equilibrium was reached, the gaseous solution was subdivided into 2.6 ml quantities and placed into 3 ml glass ampules which had been purged with the same gas mixture used in bringing the solution to equilibrium. The filled ampules were heat-sealed.

The control liquid had an appearance of a hemoglobin solution and showed the corresponding hemoglobin value equivalents as the following table:

|  | THb | $O_2Hb$ % | $O_2SAT$ % | COHb % | MetHb % | $O_2Ct$ | Vol % $O_2$ |
| --- | --- | --- | --- | --- | --- | --- | --- |
| ACIDOSIS (I) | | | | | | | |
| Corning 2500 | 9.0 g ± 0.5 g/100 ml | | −43 ± 3 | 70 ± 5 | 63 ± 5 | −5.3 ± 0.3 | |
| IL 282 | 5.5 ± 0.5 | −38 ± 3 | | 112 ± 5 | 0.9 ± 0.2 | | −2.9 ± 0.3 |
| Normal (II) | | | | | | | |
| Corning 2500 | 14. ± 0.5 | | −40 ± 3 | 65 ± 5 | 64 ± 5 | −7.5 ± 0.4 | |
| IL 282 | 8.8 ± 0.5 | −35 ± 3 | | 101 ± 5 | 6.9 ± 0.5 | | −4.2 ± 0.3 |
| Alkalosis (III) | | | | | | | |
| Corning 2500 | 18 ± 0.5 | | −39 ± 3 | 64 ± 5 | 64 ± 5 | −9.4 ± 0.4 | |

-continued

|  | THb | O$_2$Hb % | O$_2$SAT % | COHb % | MetHb % | O$_2$Ct | Vol % O$_2$ |
| --- | --- | --- | --- | --- | --- | --- | --- |
| IL 282 | 11.5 ± 0.5 | −32 ± 3 |  | 93 ± 5 | 11.9 ± 0.5 |  | −5.0 ± 0.3 |

The formulated liquid also had three levels of concentration of sodium and potassium as measured by the following different models of ion selective electrode instrumentation:

|  | Acidosis (I) | Normal (II) | Alkalosis (III) |
| --- | --- | --- | --- |
| Na |  |  |  |
| Corning 902 | 120 ± 3 mM | 140 ± 3 mM | 165 ± 4 mM |
| 614 | 120 ± 3 mM | 140 ± 3 mM | 165 ± 4 mM |
| Nova - 1 | 120 ± 3 mM | 140 ± 3 mM | 160 ± 4 mM |
| IL-501 | 120 ± 3 mM | 140 ± 3 mM | 160 ± 4 mM |
| K |  |  |  |
| Corning 902 | 3.0 ± 0.3 mM | 5.0 ± 0.3 mM | 7.4 ± 0.4 mM |
| 614 | 3.0 ± 0.3 mM | 5.0 ± 0.3 mM | 7.4 ± 0.4 mM |
| Nova - 1 | 3.0 ± 0.3 mM | 5.0 + 0.3 mM | 7.0 ± 0.4 mM |
| IL-501 | 3.0 ± 0.3 mM | 5.0 ± 0.3 mM | 7.0 ± 0.4 mM |

The ampuled formulated liquid has the corresponding values of pH, pCO$_2$, and pO$_2$ for the blood gas analyzers.

|  | Acidosis (I) | Normal (II) | Alkalosis (III) |
| --- | --- | --- | --- |
| pH (unit) | 7.15 (7.10–7.20) | 7.4 (7.38–7.42) | 7.6 (7.58–7.62) |
| pCO$_2$ mm Hg | 70 (66–72) | 40 (38–42) | 22 (20–24) |
| pO$_2$ mm Hg | 60 (58–67) | 102 (100–104) | 150 (145–155) |

Those values were measured at 37° C. The ampules containing formulated liquid can be heat sterilized at 15' PSI for 30 minutes for long term shelf life.

EQUIVALENTS

Those skilled in the art will recognize, or be able to ascertain using no more than routine experimentation, many equivalents to the specific embodiments of the invention described herein. Such equivalents are intended to be encompassed by the following claims.

For example, it will be understood by one having ordinary skill in the art that other dye combinations can be used which can absorb light as hemoglobin does. This invention is not limited to the illustrated examples of dye combinations.

I claim:

1. A multiple liquid control standard comprising an aqueous solution useful as a control for blood gas instrumentation systems buffered by a buffering agent to a pH of from about 7.1 to about 7.7 and containing sufficient bicarbonate ions to provide a pCO$_2$ from about 15 to about 80 mm Hg, gaseous oxygen to provide a pO$_2$ of from about 50 to about 400 mm Hg retained, absorbance means to provide a control test which corresponds to a predetermined level of hemoglobin and hemoglobin fractions and salts of electrolytes to provide ions selected from the group consisting of ionic lithium, ionic calcium, ionic sodium and ionic potassium, said composition providing a control test for a corresponding ion selective electrode systems.

2. The liquid control standard as recited in claim 1, wherein said liquid control standard contains a predetermined concentration of Na, K, Li, and Ca ions so that the control standard can be used to test an ion selective electrode instrumentation system which measures the amount of Na, K, Li, and Ca ions present in blood.

3. A multiple liquid control standard as in claim 2, wherein the pH ranges from about 7.10 to about 7.20, the pCO$_2$ ranges from about 60 to about 70 mm Hg, the pO$_2$ ranges from about 50 to about 65 mm Hg, and the ion concentrations and the absorbacce means simulate blood having a low level of total hemoglobin.

4. A multiple liquid control standard as in claim wherein the pH ranges from about 7.35 to about 7.45, the pCO$_2$ ranges from about 35 to about 45 mm Hg, the pO$_2$ ranges from about 95 to about 110 mm Hg, and the ion concentrations and the absorbance means simulate blood having a normal level of total hemoglobin.

5. A multiple liquid control standard as in claim 2, wherein the pH ranges from about 7.55 to about 7.65, the pCO$_2$ ranges from about 15 to about 25 mm Hg, the pO$_2$ ranges from about 140 to about 160mm Hg, and the ion concentrations and the absorbance means simulate blood having a high level of total hemoglobin.

6. A multiple control standard for use in the quality assurance of blood analysis instrumentation systems, said liquid control standard being able to act as a control standard for blood gas instrumentation systems measuring pH, pCO$_2$ and pO$_2$ of blood, as a control standard for a co-oximeter measuring the amount of total hemoglobin present in the blood and the relative amounts of other hemoglobin fractions present in the blood, and a control standard for ion selective electrode instrumentation systems measuring the concentration of Na, K, Li and Ca ions in the blood, wherein the control standard is an aqueous solution buffered by a buffering agent to a pH of from about 7.1 to about 7.7 and containing sufficient bicarbonate ion to provide a pCO$_2$ from about 15 to about 80 mm Hg, gaseous oxygen to provide a pO$_2$ of from about 50 to about 400 mm Hg retained, absorbance means to provide a control test which corresponds to a predetermined level of hemoglobin and hemoglobin fractions, said absorbance means being comprised of Acid Red Dye #27 (CI 16185), Acid Yellow Dye #23 (CI 19140) and Acid Blue Dye #9 (CI 42090), and salts of Na, K, Li and Ca to provide a control test for a corresponding ion selective electrode instrumentation system.

7. A multiple control standard for use in the quality assurance of blood analysis instrumentation systems, said liquid control standard being able to act as a control standard for blood gas instrumentation systems measuring pH, pCO$_2$ and pO$_2$ of blood, as a control standard for a co-oximeter measuring the amount of total hemoglobin present in the blood and the relative amounts of other hemoglobin fractions present in the blood, and a control standard for ion selective electrode instrumentation systems measuring the concentration of Na, K, Li and Ca ions in the blood, wherein the control standard is an aqueous solution buffered by a buffering agent to a pH of from about 7.1 to about 7.7 and containing sufficient bicarbonate ion to provide a pCO$_2$ from about 15 to about 80 mm Hg, gaseous oxygen to provide a pO$_2$ of from about 50 to about 400 mm Hg retained, absorbance means to provide a control test which corresponds to a predetermined level of hemoglobin and hemoglobin fractions, said absorbance means being comprised of Ponceau 3R Red Dye (CI 16155) and Acid Blue Dye #9 (CI 42090).

* * * * *

UNITED STATES PATENT AND TRADEMARK OFFICE
CERTIFICATE OF CORRECTION

PATENT NO. : 4,843,013

DATED : June 27, 1989

INVENTOR(S) : Ching Chiang

It is certified that error appears in the above-identified patent and that said Letters Patent is hereby corrected as shown below:

Claim 3, line 5, change "absorbacce" to ---absorbance---.

Claim 4, line 1, after "claim", insert ---2---.

Signed and Sealed this

Eighth Day of May, 1990

Attest:

HARRY F. MANBECK, JR.

Attesting Officer — Commissioner of Patents and Trademarks